(12) United States Patent
Madio et al.

(10) Patent No.: US 7,486,070 B2
(45) Date of Patent: Feb. 3, 2009

(54) DEVICES, SYSTEMS AND METHODS FOR ASSESSING POROUS MEDIA PROPERTIES

(75) Inventors: David P. Madio, Sugar Land, TX (US); David Linton Johnson, Somerville, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 59 days.

(21) Appl. No.: 11/612,010

(22) Filed: Dec. 18, 2006

(65) Prior Publication Data
US 2008/0143330 A1 Jun. 19, 2008

(51) Int. Cl.
*G01V 3/00* (2006.01)
(52) U.S. Cl. ...................................... 324/303; 324/318
(58) Field of Classification Search .................. 324/303
See application file for complete search history.

(56) References Cited

U.S. PATENT DOCUMENTS

| | | | |
|---|---|---|---|
| 4,724,385 A | 2/1988 | Vail, III | |
| 5,428,291 A * | 6/1995 | Thomann et al. | 324/303 |
| 6,528,995 B1 * | 3/2003 | Speier et al. | 324/303 |
| 6,933,719 B2 | 8/2005 | Thomann et al. | |

FOREIGN PATENT DOCUMENTS

WO 02093126 A3 11/2002

OTHER PUBLICATIONS

Brie et al., "Quantitative Formation Permeability Evaluation from Stoneley Waves", SPE 49131, Sep. 27-30, 1998.
Denk et al., "Oscillatory Flow in the Cochlea Visualized by a Magnetic Resonance Imaging Technique", Proc. Natl. Acad. Sci. vol. 90, pp. 1595-1598, Feb. 1993.
Miller et al., "Spin Echo Magnetic Resonance Logging: Porosity and Free Fluid Index Determination", SPE 20561, Sep. 23-26, 1990.
Looyestijn et al., Permeability determination through NMR detection of acoustically induced fluid oscillation, Magnetic Resonance Imaging, vol. 24, 2006, pp. 1187-1201.

* cited by examiner

*Primary Examiner*—Louis M Arana
(74) *Attorney, Agent, or Firm*—James McAleenan; Vincent Loccisano; Jody Lynn DeStefanis (57) ABSTRACT

Certain embodiments are directed to devices, systems and methods for determining a penetration depth of an induced oscillation in a porous medium. In certain examples, the devices, systems and methods are designed to detect a magnetic resonance signal in the presence of an induced oscillatory fluid flow in a porous medium to determine penetration depth of the induced oscillation in the porous medium. In some examples, the mobility of a fluid in the porous medium may be determined from the determined penetration depth.

33 Claims, 8 Drawing Sheets

DEVICES, SYSTEMS AND METHODS FOR ASSESSING POROUS MEDIA PROPERTIES

FIELD OF THE TECHNOLOGY

Embodiments of the technology disclosed herein relate generally to devices, systems and methods configured to determine a penetration depth of an induced oscillation in a porous medium. More particularly, certain embodiments of the technology disclosed herein relate to devices, systems and methods that may determine a penetration depth of an induced oscillation using magnetic resonance techniques.

BACKGROUND

It is difficult to measure the physical properties of a fluid in a potential petroleum bearing rock formation. The use of a logging method to measure mobility (permeability divided by viscosity) typically requires measuring of a fluid flow rate simultaneously with a pressure gradient. These measurements may be difficult to do especially in downhole applications.

Typical penetration depths for petroleum bearing rock formation may range from about 0.1 mm to about 20 cm, more particularly about 1 mm to about 10 cm, e.g., for a rock formation saturated with water-like fluids. The methods, systems and devices may be used in downhole applications, or in situations where a core sample is taken, the core sample may be brought uphole and analyzed using the methods, systems and devices disclosed herein on or off-site, e.g., in a laboratory using an electromagnet or superconducting NMR.

There are many drawbacks of existing techniques of measuring physical properties of porous media such as, for example, a potential petroleum bearing rock formation. For example, mudcake barriers may cause unknown effects and give aberrant results. Leakage around probes or unknown effects of empirically based correlations, e.g., NMR decay rate measurements, estimates based on mineralogy, can provide inaccurate results. Such problems make physical property measurements, such as mobility, of a potential petroleum bearing rock formation difficult to accomplish, particularly using a logging method.

It is an object of the present invention to address these difficulties.

SUMMARY

In accordance with a first aspect, a method of determining a penetration depth in a porous medium is provided. In certain examples, the method comprises inducing an oscillation in a pore fluid within the porous medium, and determining a penetration depth of the induced oscillation from a magnetic resonance signal. In some examples, magnetic resonance imaging of the induced oscillation may be used to determine a penetration depth of the induced oscillation.

In accordance with an additional aspect, a method of determining a penetration depth in a porous medium is disclosed. In certain examples, the method comprises determining the penetration depth of an induced oscillatory fluid flow in the porous medium using a magnetic resonance signal from each of two or more spatially discrete points in the porous medium. In certain examples, magnetic resonance imaging may be used to determine penetration depth. For purposes of the technology disclosed herein, imaging refers to measuring a quantity or parameter at two or more spatially distinct points. In some examples, an image may be generated, whereas in other examples no image is generated but, instead, a value at each of two or more spatially distinct points may be used to determine the penetration depth. In some embodiments described herein, a one-dimensional image such as, for example, in the direction radially outward from the borehole, may be referred to, in certain instances, a profile. In certain embodiments, the method may include applying a radio frequency (RF) pulse to the porous medium (and any fluid(s) therein) to tip nuclear spins and applying a perturbation to the porous medium to generate the induced oscillation in the porous medium. In some examples, the method may also include applying a magnetic field gradient having substantially the same frequency as the applied perturbation. In some examples, the method may also include applying a magnetic field gradient having a frequency that is substantially the same as, or an integer multiple thereof, of the applied perturbation frequency optionally in conjunction with RF pulses. In yet other examples, the magnetic field gradient may be static and RF pulses may be applied at twice the frequency of the perturbation frequency. In certain examples, the method may further include imaging the induced oscillation with a magnetic resonance device. In yet other examples, the method may also include determining a mobility of a fluid in the porous medium from the determined penetration depth.

In accordance with another aspect, a method of determining formation productivity is disclosed. In certain examples, the method includes disposing a magnetic resonance device in a borehole near a formation, inducing an oscillation in a pore fluid within the formation; and determining penetration depth of the induced oscillation in the formation using the magnetic resonance device.

In accordance with an additional aspect, a downhole tool is provided. In certain examples, the downhole tool comprises a device that is constructed and arranged to provide a perturbation to induce an oscillation in a pore fluid within a porous medium. In some examples, the downhole tool also includes a magnetic resonance device constructed and arranged to permit determination of a penetration depth of the induced oscillation. In other examples, the downhole tool may also include a processing device electrically coupled to the magnetic resonance device, the processing device configured to determine mobility of a fluid in the porous medium from the imaged penetration depth.

In accordance with another aspect, a system for assessing formation productivity is disclosed. In certain examples, the system includes a magnet for producing a static magnetic field. In other examples, the system may also include a transmitter/receiver, which may be a single device or two or more devices, for applying a RF pulse and for detecting a magnetic resonance signal that represents a penetration depth of an oscillation induced by application of a perturbation. In certain examples, the system may also include a device for applying a perturbation to induce an oscillation in a pore fluid within the formation. In certain examples, the system may also include a device for providing a magnetic field gradient. In some examples, the system may include a processing device electrically coupled to the magnetic resonance device, the device for applying the perturbation and the device for providing a magnetic field gradient.

Additional features, aspect, embodiments and examples of the technology are described in more detail below.

BRIEF DESCRIPTION OF THE FIGURES

Certain embodiments are described below with reference to the accompanying figures in which.

Certain features or dimensions shown in the figures may have been enlarged, distorted, altered or otherwise shown in a non-conventional manner to facilitate a better understanding of the technology disclosed herein and to provide a more user-friendly version of the figures.

DETAILED DESCRIPTION

Certain embodiments of the devices, systems and methods disclosed herein provide for measurements of porous media not previously achieved with existing methods. Embodiments of the devices, systems and methods disclosed herein may be used to identify porous formations with high mobility to identify productive well sites that may be used to extract hydrocarbon fuel sources such as, for example, natural gas and petroleum products. In certain examples, the methods, systems and devices disclosed herein may be used to determine penetration depths of oscillations in petroleum bearing rock formations A potential petroleum bearing rock formation is made of up two solid components. The first component is the rock matrix, and the second component is dry clay. The total porosity may be measured by a density logging tool and is defined as the difference between the total volume and the solid portion. Total porosity includes clay bound water, movable water, bound water, petroleum, natural gas and possibly other bound or free fluids such as hydrocarbons.

Unlike existing methods, which typically measure a change in relaxation times, e.g., $\Delta T_2$, to try to deduce fluid flow properties, embodiments of the devices, systems and methods disclosed herein determine the penetration depth of an induced oscillation in a porous medium, such as a rock formation. Certain examples disclosed herein are directed to monitoring the spatial dependence of an induced oscillation resulting from application of an external perturbation. In certain embodiments, measurement of the absolute magnitude of the induced oscillation is not needed, and the rate at which the oscillation varies spatially as probing depth increases may be monitored. In certain examples described herein, the depth dependence of the induced oscillation may be monitored using a magnetic field gradient in combination with detection of a magnetic resonance signal or by using magnetic resonance imaging.

In accordance with certain examples, a method of determining penetration depth of an induced oscillation in a porous medium is disclosed. In certain examples, a perturbation may be applied to the porous medium to exert a force on the medium and induce an oscillation of a pore fluid in the medium. The exact nature of the oscillation induced in the pore fluid may vary depending on the nature of the perturbation waveform. For example, a sinusoidal perturbation may be applied to induce a sinusoidal waveform. In certain examples, a flow is induced in a pore fluid, and the induced flow may be measured and used to determine penetration depth. The induced flow may be in a pore fluid that comprises water, drill fluid, mud filtrate, petroleum, natural gas or other fluids present in or near the formation. While it is desirable to determine mobility of petroleum, natural gas or other fuels in a formation, the mobility of such species may be indirectly determined or inferred by determining mobility of fluids such as water or mud filtrate present in the formation. Thus, the oscillations described herein are not necessarily induced in any petroleum, hydrocarbon or other fuel sources present in the formation.

In accordance with certain examples, the oscillation may be induced and measurements may be made during a single cycle or after multiple cycles. For example, about 10-50 oscillation cycles may be applied to establish a steady state prior to NMR measurements to determine penetration depth. In some examples, about 40-50 oscillations cycles, e.g., 44 or 45 oscillation cycles, may be applied during motion encoding and prior to any NMR spatial measurements. The applied perturbation that induces the oscillation may remain on during the NMR spatial measurements or may be switched off during the NMR spatial measurements. It will be within the ability of the person of ordinary skill in the art, given the benefit of this disclosure, to select suitable numbers of oscillations for use in the methods, systems and devices disclosed herein.

In accordance with certain examples, a flow may be induced in the fluid using many common acoustic techniques and illustrative techniques are discussed herein. The penetration depth of the induced oscillation varies as a function of fluid viscosity, porosity, permeability and effective bulk modulus of a fluid in the porous medium according to Equation 1 below.

$$\kappa = \sqrt{\frac{\omega \eta \phi}{2 k K_f^*}} \quad [1]$$

In Equation 1, $\kappa$ represents the spatial dependence with $1/\kappa$ being the penetration depth of the induced oscillation. $\eta$ represents the viscosity of the pore-fluid, $\phi$ represents the porosity, k is the permeability and $K^*_f$ is the effective bulk modulus of the pore-fluid, as corrected according to the known properties of the porous medium. $\omega$ represents the angular frequency of the external perturbation. The quantities $K^*_f$, $\phi$ and $\omega$ may all be determined by conventional logging methods or are otherwise known. For example, $K^*_f$ may be determined by a combination of acoustic, electrical, and nuclear logging measurements, $\phi$ may be determined by conventional crossplot of neutron/density logging measurements and $\omega$ is known or selected by a user.

In accordance with certain examples, based on the relationship shown in Equation [1], a determination of penetration depth $1/\kappa$ may then be used to determine the mobility, which is the permeability divided by the viscosity ($k/\eta$). Rock formations having a high mobility are desirable sites for producing wells. In particular, the devices, systems and methods disclosed herein may be used to identify rock formations having a high mobility, which may be selected first to produce wells for extracting hydrocarbon fuel sources.

In accordance with certain examples, a perturbation may be provided to introduce a temporal oscillation, at an angular frequency $\omega$, in the porous medium. This oscillation may take the form of an induced fluid flow in the porous medium as the perturbation may induce an oscillatory fluid flow in fluid occupying the pores of the rock formation. The perturbation may be a sound wave, a pressure wave or other perturbation that can induce an oscillation at least temporarily. In certain embodiments, an acoustic source located on a conventional logging sonde may be used to provide the perturbation. In another example, a packer device may be used to provide the perturbation. Additional devices for inducing a temporally oscillating flow will be readily selected by the person of ordinary skill in the art, given the benefit of this disclosure. For example, a sound generator, a pressure generator, a transducer, a transducer coupled to a Helmholtz resonator, a speaker, a vibrating plate, a piezoelectric device, a resonator tube coupled to a gas source may be used to provide a perturbation that can induce an oscillation of a fluid within the rock formation. Additional suitable devices for applying a perturbation to a rock formation will be readily selected by the person of ordinary skill in the art, given the benefit of this disclosure.

In accordance with certain examples, the exact frequency at which the perturbation is applied is not critical provided that the induced oscillation is capable of being detected using magnetic resonance. In certain examples, the frequency may vary from about 500 Hz to about 5 kHz, more particularly about 750 Hz to about 2 kHz, e.g., about 1 kHz. Any frequency may be used, however, so long as the NMR pulse sequence, which may include RF pulses and an applied magnetic field gradient that may be maintained at a fixed phase relative to perturbation frequency, provides a magnetic resonance signal that may be detected. As discussed herein, the frequency of the applied magnetic field gradient may be substantially the same as the frequency of the applied perturbation or may be an integer multiple of the frequency of the applied perturbation, e.g., twice or three times the frequency of the applied perturbation frequency. It will be recognized by the person of ordinary skill in the art, given the benefit of this disclosure, that the frequency of the gradient may be slightly less than, e.g., 90-95%, or greater than 105-110%, of the perturbation frequency, in the methods, systems and devices disclosed herein. In certain embodiments, the magnetic field gradient frequency may be any frequency that encodes motion, as discussed in more detail below.

In accordance with certain examples, application of the perturbation may take numerous forms. In certain examples, the perturbation is applied in a continuous manner such that the perturbation is always incident on the rock formation. Continuous application of the perturbation may allow an induced oscillation to reach a steady state and provide for a more accurate representation of the penetration depth. In other examples, the perturbation may be applied in a discrete or pulsed manner. For example, the perturbation may be applied for a selected time period followed by a delay period before reapplication of the perturbation. In certain examples, the perturbation may be applied before and during motion encoding, but turned off during spatial encoding. In certain examples, baseline images made without the perturbation may be interspersed with images made with the perturbation.

In certain examples, mudcake built-up on the porous medium may act to impede or retard the oscillation. An oscillation can still be induced, however, even in the presence of mudcake, and the penetration depth of the induced oscillation is believed to be substantially independent of the mudcake properties. The devices, systems and methods disclosed herein may be particularly useful in situations where excessive mudcake buildup hampers conventional measurements used to identify mobility of fluids or permeability of rock formations.

In accordance with certain examples, a perturbation may be provided to the porous medium by stimulation at an angular frequency ω. If the frequency of the stimulation is below the Biot crossover frequency, the displacement of fluid by the oscillation may be represented by Equation 2 below where u(x,t) represent the distance fluid is displaced.

$$u(x,t) = A \exp(-\kappa x)\cos(\kappa x - \omega t + \delta) \quad [2]$$

In Equation 2, there is a decaying component represented by the envelope function (exp(-κx)) and an oscillating component represented by the cosine portion of Equation 2. δ is an arbitrary phase factor, which may be chosen for convenience. The amplitude A in Equation 2 depends, at least in part, on the properties of any possible mudcake, as a larger and/or stiffer mudcake may act to reduce the value of A relative to the value A would hold if the mudcake were thinner and/or less stiff. If the penetration depth is measured in the porous medium, however, the effects of any surface mudcake are believed to be negligible.

It will be appreciated by the person of ordinary skill in the art, given the benefit of this disclosure, that even though the illustrative model discussed below is described in the context of a low frequency limit, the methods, systems and devices disclosed herein are equally applicable and useful in models based on more complex models of poroelasticity. In particular, it will be within the ability of the person of ordinary skill in the art, given the benefit of this disclosure, to apply and/or use the methods, systems and devices disclosed herein with less simplified poroelasticity models and using conventional logging methods to determine, for example, any desirable parameters that may be useful in determining mobility of a fluid in a porous medium and/or permeability of a porous medium.

Figure 1:
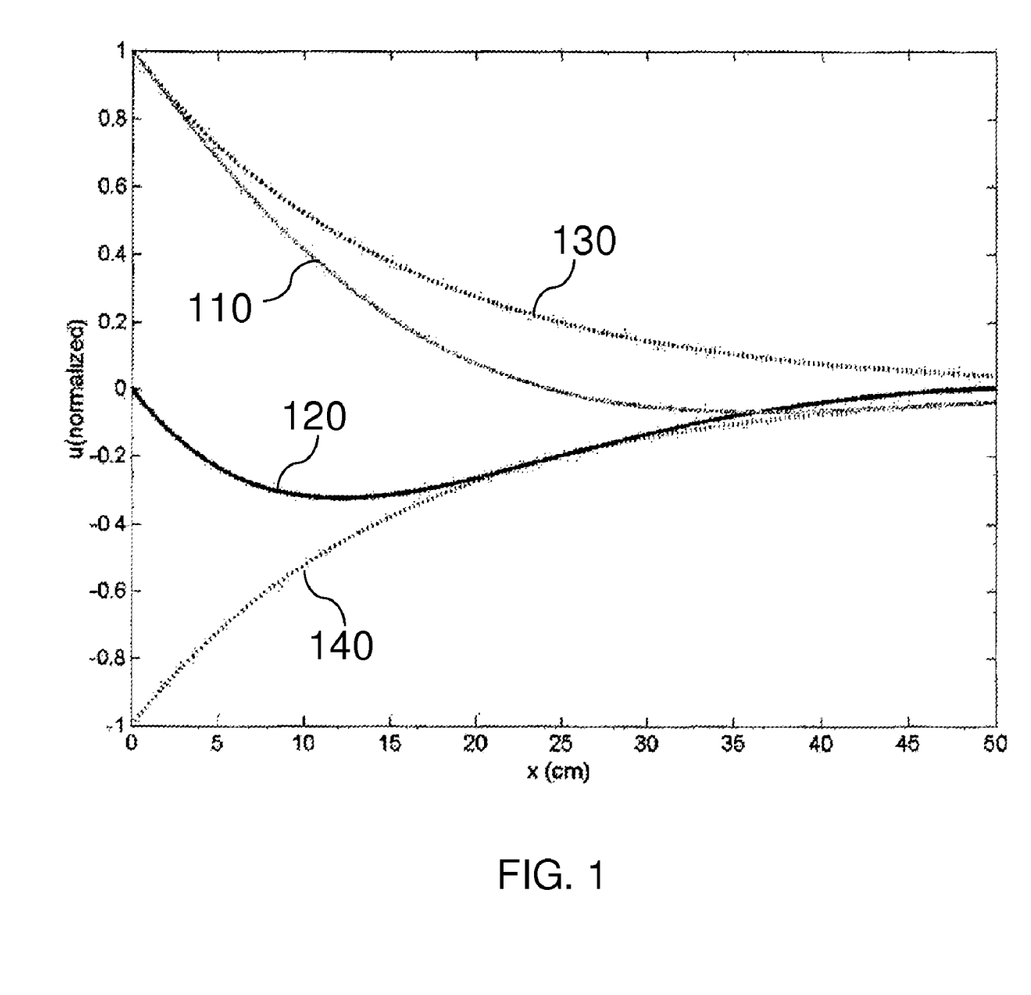
FIG. 1 is a graph of oscillating fluid displacement versus distance, in accordance with certain examples.

In accordance with certain examples, a representative spatial variation (u/A) for a specific set of parameters is shown in FIG. 1. The curves shown in FIG. 1 were generated using Equations 1 and 2 and by assuming that the permeability was 10 Darcy, the porosity was 30%, the frequency was 1000 Hz, and the fluid was water. The two solid curves 110 and 120 correspond to (δ=0, t=0) and to (δ=0, t=3π/2ω), respectively. The two dotted curves 130 and 140 are the envelope functions ±exp(-κx). The penetration depth is the depth at which the amplitude of the motion has decayed to about 1/e (i.e., 36.8%) of an initial value. It will be recognized by the person of ordinary skill in the art, given the benefit of this disclosure, that it is not necessary to measure the exact value of the penetration depth. For example, two or more spatially discrete values that are each greater than 1/e may be determined and used to infer the penetration depth using the exponential decay of the signal. In addition, the initial value of the amplitude of motion is typically selected by a user and the value may change from measurement to measurement. The initial value may be the value at a surface of the rock formation, or a value at a selected distance, e.g., 1 inch, 2 inches, etc., into the rock formation. In addition to the displacement curve represented by Equation 2 above, there is also a displacement that may be attributed to an acoustic wave in the porous medium. This length, however, is much longer, e.g., several meters, than the penetration depths determined using the devices, systems and methods disclosed herein.

In accordance with certain examples, the spatial dependence of the displacement may be measured using nuclear magnetic resonance (NMR) techniques, e.g., magnetic resonance imaging techniques. In certain examples, a portion of the porous medium may be placed within a static magnetic field to align the nuclear spins with the magnetic field, here defining the z-direction. The spins in the system may then be tipped into the x-y plane by application of a π/2 pulse, e.g., a $90_x$ pulse or a $90_y$ pulse. An oscillatory magnetic field gradient g(t) may then be applied to encode fluid motion and may be represented by Equation 3.

$$g(t) = g_o \cos \omega t \quad [3]$$

In certain examples, the frequency ω of the field gradient is the same frequency as the frequency of the applied perturbation. Though the gradient waveform is shown in Equation 3 as a cosine function, the gradient waveform may also take other forms including, but not limited to, an essentially square wave and a trapezoidal wave. Additionally, the gradients may be pulsed in a variety of waveforms in combination with RF pulses. In certain examples, half-cycle monopolar square gradient pulses, which may be briefly off for 180° RF pulses that refocus background inhomogeneity and reduce diffusion effects, may be used. In the case of monopolar square gradient pulses, the gradient period may be half that of the perturbation frequency. In other examples, single-cycle square gradient pulses, which may be briefly off for a 180° pulse then switch on again but phase inverted may be used in the methods, systems and devices disclosed herein.

In the reference frame rotating at the Larmor frequency, $\omega_o = \gamma B_o$, where γ is the gyromagnetic ratio and $B_o$ is the static magnetic field strength, the phase the spins acquire depends on their position, as defined by Equation 4.

$$\Phi(x, t) = \gamma \int_0^t \Delta B_o[x(t'), t']dt' \cong \gamma \int_o^t g(t')[x + u(x, t')]dt' \quad [4]$$

Based on Equations 2, 3 and 4, the phase of the spins has components oscillating at frequencies ω and 2ω as well as a component Φo(t), which increases linearly with time, as represented by Equation 5.

$$\Phi_o(t) = \frac{1}{2}\gamma A g_o \exp(-\kappa x)\cos(\kappa x + \delta)t \quad [5]$$

By imaging the penetration depth, 1/κ, in the presence of a magnetic field gradient that is phase locked to substantially the same frequency as the applied perturbation, or an integer multiple thereof, the mobility of the porous medium may be determined using Equation 1. In particular, the penetration depth of a slow compressional wave in the induced oscillation may be determined and used to determine the mobility of the porous medium. In certain examples, two parameters are provided or determined for every spin or group of spins. The first parameter is location of the spin, and the second parameter is the degree of movement of the spin. Motion is encoded by a phase-locked oscillating gradient or an equivalent thereof, with an illustrative equivalent being a static gradient and a series of 180° pulses. Battling against relaxation and diffusion, this process may be repeated to acquire greater phase. Position of the spins may be encoded using traditional NMR spin-warp imaging, e.g., application of a gradient, followed by a 180° pulse, followed by a read gradient. These two types of encoding may be performed sequentially or simultaneously. For example, motion may first be encoded followed by position encoding. In some examples, phase build may be monitored by acquiring echoes at a plurality of times during the phase encoding.

In certain examples, the methods, systems and devices disclosed herein may use two or more different perturbation frequencies. In certain examples, the method comprises determining the fluid mobility by varying the frequency of the perturbation and measuring the NMR signal at a fixed location. In these embodiments, encoding the fluid motion may include some combination of RF pulses and/or magnetic field gradient pulses that are phase-locked to a multiple of the perturbation frequency. Based on Equation 1 above, κ varies as the square root of the angular frequency ω, and for a pair of measurements at different frequencies $\omega_1$ and $\omega_2$, the mobility may be represented by Equation 6

$$\frac{k}{\eta} = \left[\frac{(\sqrt{\omega_2} - \sqrt{\omega_1})x}{\ln(y_1/y_2)}\right]^2 \frac{\varphi}{2K_f^*} \quad [6]$$

where x is the position of the measurement relative to a point whose amplitude of motion is substantially independent of the perturbing frequency, e.g., the borehole wall, y is the NMR-measured amplitude of fluid displacement at position x, and the subscripts 1 and 2 refer to a measurement $y_1$ at a frequency $\omega_1$ and a measurement $y_2$ at a frequency $\omega_2$. If the fluid viscosity is known or estimated, permeability may be derived. In addition, the person of ordinary skill in the art, given the benefit of this disclosure, may derive other methods of determining mobility from two or more measurements made with varying perturbation frequencies.

In accordance with certain examples, two or more values at different depths may be measured and used to determine the penetration depth. For example, different depths of investigation within a rock formation may be used to determine penetration depth. In particular, when an MRX device, or MR Scanner (commercially available from Schlumberger), or a comparable device, is used, different depths may be selected by varying the resonance frequency of the device. An illustrative MRX device is described in more detail below, and other suitable devices include, but are not limited to MR Explorer, or MREX (available from Baker-Hughes) and MRIL (available from Haliburton).

In accordance with certain examples, the penetration depth of the oscillation, e.g., the decaying component of the spatially varying motion, may be imaged by numerous different methods. Illustrative methods are described in "Spin Echo Magnetic Resonance Logging: Porosity and Free Fluid Index Determination," M. N. Miller et al. Soc. Petrol. Eng., Paper No. 20561. Another illustrative method uses some portion, or all of, a Carr, Purcell, Meiboom and Gill (CPMG) pulse sequence. In one method, a pulse sequence similar to that described in Denk et al., *Proc. Natl. Acad. Sci.*, 90, 1595-1598 (1993) may be used to image movement of the induced flow. A magnetic field gradient may be phase-locked to a multiple of, or substantially the same as, the frequency of the external perturbation to generate a magnetic resonance image of the induced flow that is correlated with the perturbation. Spins that move with the external perturbation experience a slightly different average magnetic field than the static magnetic field. This slight difference results in accumulation of an additional phase shift by these spins proportional to their local experience of the external perturbation.

In accordance with certain examples, a pulse sequence suitable for imaging includes a spin echo sequence in which the spatial-encoding and read gradients may be applied around a π refocusing pulse. One or more oscillating field gradients may be applied in either the x, y or z direction to measure different components of the motion. The spatial read gradient is typically applied along the direction of the slice to be imaged or detected while the motion-encoding gradient is applied in the direction of motion. In certain examples, a gradient echo sequence may be used for detection or imaging in place of a spin echo sequence. In certain examples, the oscillating gradient may be of an opposite phase before and after the π refocusing pulse. Variation of the phase between the oscillating gradient and the external perturbation allows for a determination of the phase shift between the external perturbation and the induced oscillation.

In accordance with certain examples, the induced oscillation, and consequently the penetration depth, may be imaged by subtracting two data sets. The first data set may be taken with the external perturbation having a first phase, and the second data set may be taken with the phase of the external perturbation inverted. Signals from stationary spins are generally not affected by the phase inversion and cancel out in the difference image. Signals resulting from oscillatory motion induced by the external perturbation add and are visible in the difference image. The sum of the data sets provides a conventional magnetic resonance imaging data set or model. Which, may include an image that may be used to determine the penetration depth of the oscillation, e.g., an induced oscillatory fluid flow.

In accordance with certain examples, the exact duration of the oscillating field gradient may vary. In certain examples, the duration may be longer before application of the π refocusing pulse than the duration of the gradient applied after the π refocusing pulse, whereas in other examples, the duration may be shorter before application of the π refocusing pulse than the duration of the gradient applied after the π refocusing pulse.

In accordance with certain examples, a series of perturbations and images may be measured and averaged to reduce noise in the images. In certain examples, the data obtained from the magnetic resonance measurements may be processed prior to determination of a penetration depth. For example, one or more apodization functions, e.g., exponential functions, may be applied to reduce background noise. In another example, analyzing the difference signal may comprise fitting a function, such as a single or double exponential function or a one- or two-dimensional numerical Laplacian inversion function, to the difference signal in order to estimate a penetration depth.

Figure 2:
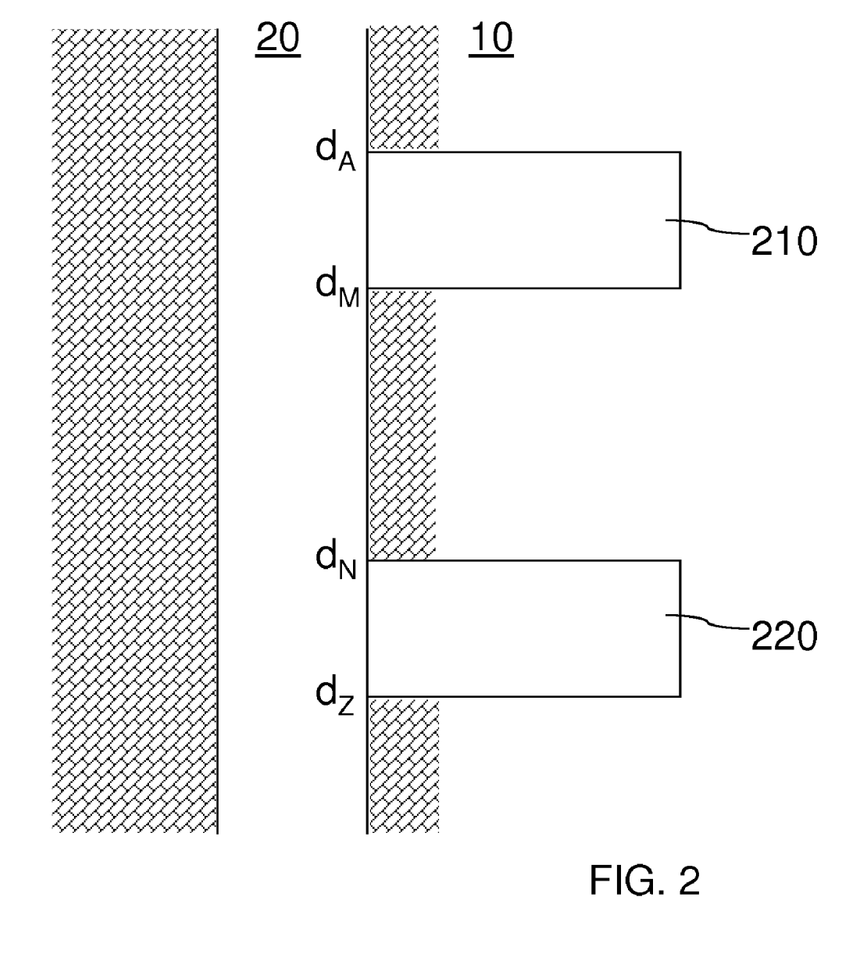
FIG. 2 is a schematic showing measurements at a locations in a borehole, in accordance with certain examples.
Figure 3:
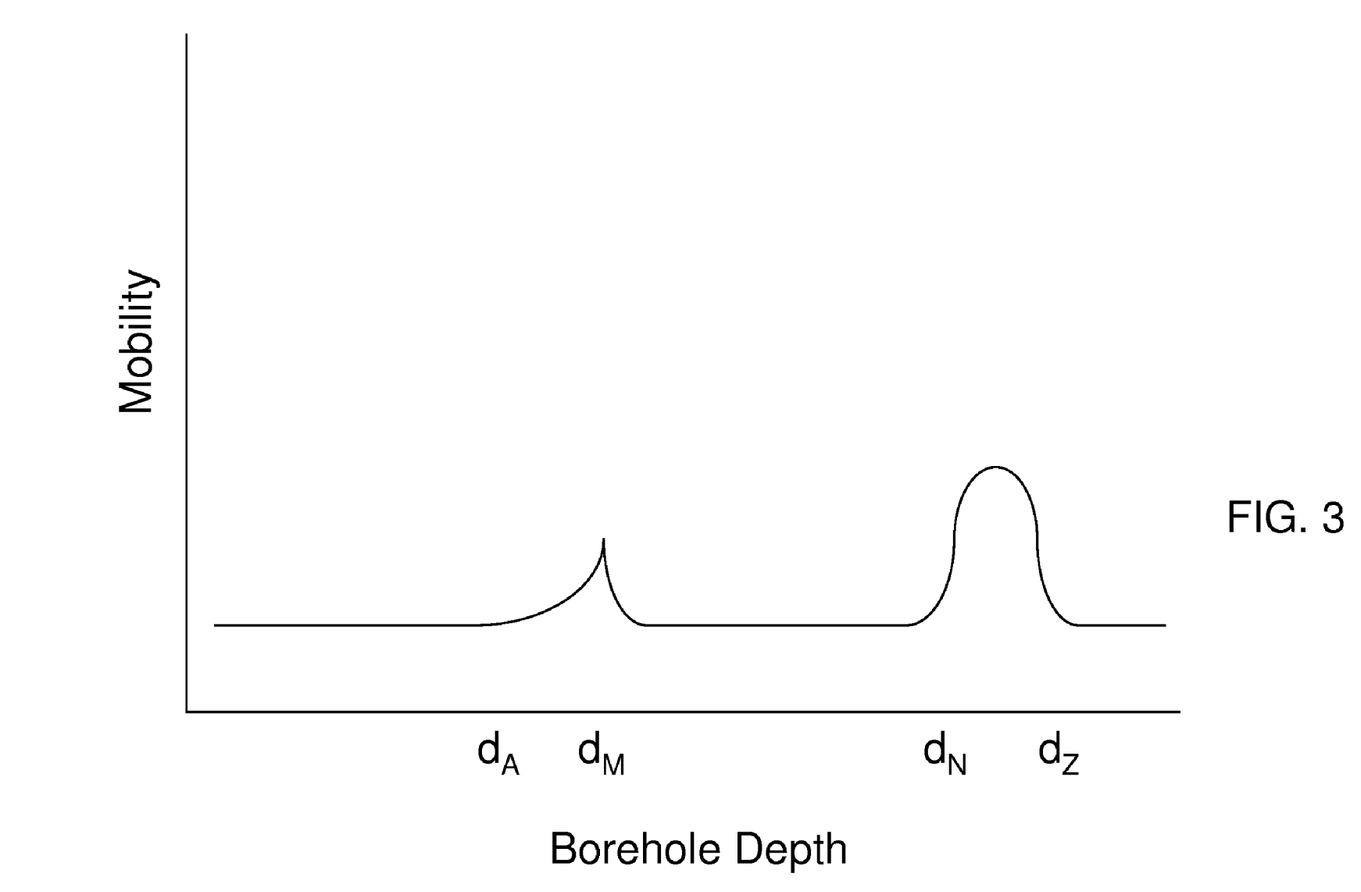
FIG. 3 is an illustrative graph of mobility versus borehole depth, in accordance with certain examples.

In accordance with certain examples, a method of determining penetration depth of an induced oscillation in a porous medium is provided. In certain examples, the method includes detecting a magnetic resonance signal in the presence of the induced oscillation. The magnetic resonance signal may be a (1) single signal or (2) an average or (3) multiple signals or a combination thereof. The magnetic resonance signal may be used to construct a mobility profile of the rock formation at various depths in the borehole. For example and referring to FIG. 2, penetration depth i.e. into the formation 15 relative to the borehole 20 of an induced oscillation in rock formations (shown schematically as rectangles 200 and 210) may be determined at various depths $d_A \ldots d_M$ and $d_N \ldots d_Z$ in the borehole. A mobility profile, such as the illustrative mobility profile shown in FIG. 3, may be constructed such that locations of the borehole where mobility is high may be produced first. For example, in the illustration shown in FIG. 3, the borehole depth $d_M$ has a high mobility and may be suitable for early production. Similarly, the entire location between depths $d_N$ and $d_Z$ has a high mobility and may be suitable for early production. Though the depth profile shown in FIGS. 2 and 3 is illustrated as vertical, horizontal profiles may also be generated in instances where horizontal drilling has taken place. Alternatively, depth may be determined by the distance the drill bit has been inserted into the borehole without regard to the direction the borehole has been drilled.

In accordance with certain examples, the oscillation may take the form of an induced oscillatory fluid flow. Without wishing to be bound by any particular scientific theory, as a perturbation is applied to the rock formation, the fluid in the pores of the rock formation are pushed on and a fluid flow at a particular frequency may be induced. The distance by which the fluid is displaced may be used, as described above, to determine penetration depth and mobility of the fluid in the rock formation. Highly porous rock formations often have higher mobilities and are more desirable for production as removal of hydrocarbon fuels is typically easier.

In accordance with certain examples, a magnetic field gradient may be applied to the induced oscillatory fluid flow at the same frequency as the applied perturbation. As discussed above, by phase-locking the frequencies of the applied perturbation and the magnetic field gradient, a difference image may be obtained and used to determine penetration depth of the induced oscillatory fluid flow. An image may be obtained at various depths within the rock formation, e.g., at various depths perpendicular to the borehole.

In accordance with certain examples, the devices, systems and methods disclosed herein may be configured for use with one or more other analytical techniques. For example, it may be desirable to analyze a fluid in a rock formation to determine viscosity of the fluid, or it may be desirable to determine the amount of light versus heavy chain hydrocarbons present in a formation. Another analytical device, such as a chromatograph, may be used in combination with the penetration depth measurements disclosed herein to provide a more complete analysis of the environment of the rock formation. Illustrative additional devices include, but are not limited to, a gas chromatograph, a liquid chromatograph, a viscometer, a measurement of fluid compressibility, or any of various optical fluid analyzers commonly used in measuring properties of rock formations, fluids and other species encountered downhole.

Figure 4A:
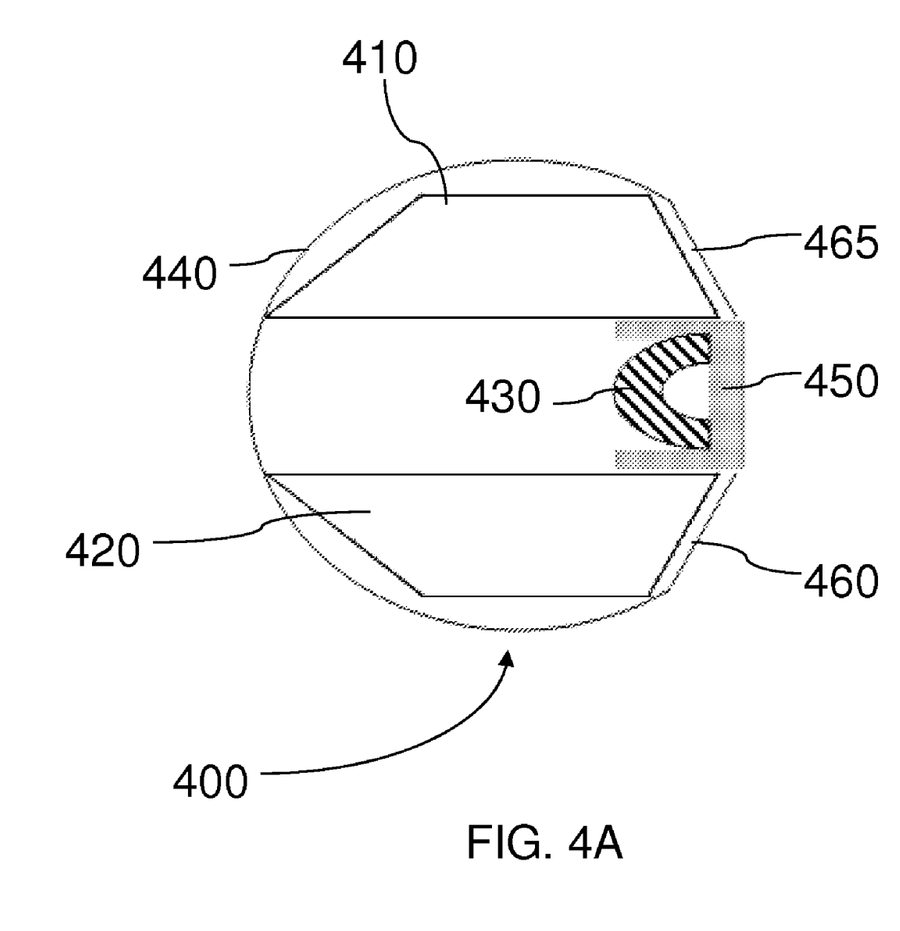
FIG. 4A is a top-view of an illustrative magnetic resonance device, in accordance with certain examples.
Figure 4B:
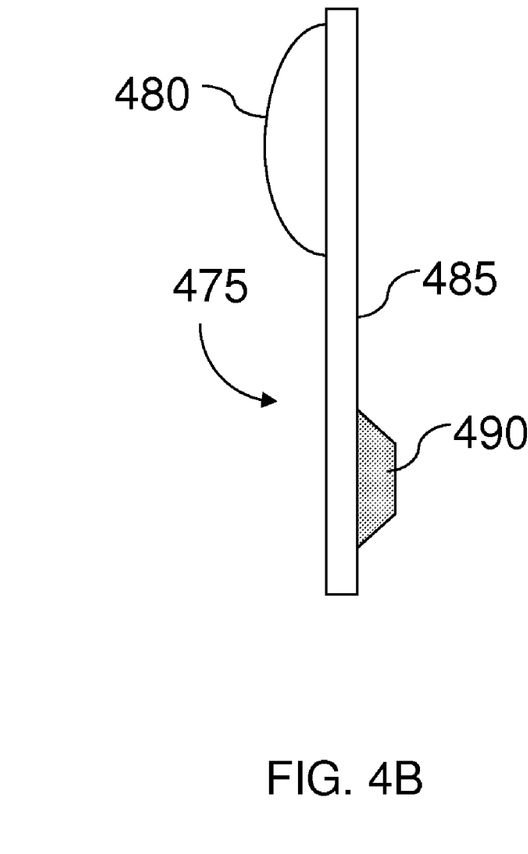
FIG. 4B is a schematic of a packaged magnetic resonance device, in accordance with certain examples.

In accordance with certain examples, a suitable device for magnetic resonance imaging is shown in FIG. 4A. The device shown in FIG. 4A is referred to in some instances herein as a pulse magnetic resonance tool. The device 400 in FIG. 4A is shown in cross-section when viewed from the top. The device 400 includes a first permanent magnet 410, a second permanent magnet 420, and an antenna 430 in a housing 440. The device may also include a wear plate 450 which typically is in contact with a side-surface of a borehole. The device may optionally include additional wear plates attached to surfaces 460 and 465. The first permanent magnet 410 and the second permanent magnet 420 provide a static magnetic field. The static magnetic field may be of a sufficient strength to provide a sampling region of about 0.5 to about 1.5 inches into the rock formation and a vertical resolution equivalent to the length of the antenna, e.g., about 2-8 inches, more particularly about 6 inches. The area immediately in front of the antenna typically does not contribute to the signal, which allows the device to operate with a certain amount of rugosity. The antenna 430 may be configured to operate as both a transmitter and a receiver. The antenna 430 may transmit pulses to tip the spins into the x-y plane using a suitable pulse sequence and may also receive pulse echoes from the formation. In certain examples, a coil may be inserted with device 400 to provide a magnetic field gradient to the rock formation. In other examples, the device 400 may include an integral coil or an additional antenna for generating a magnetic field gradient Illustrative commercially used magnetic resonance devices suitable for use with the devices, systems and methods disclosed herein include a CMR tool, produced commercially by the assignee of the instant application. In certain examples, the device shown in FIG. 4A may be mounted in a skid-type sensor package, as shown in FIG. 4B. The package 475 includes a bowspring eccentralizing arm or a powered caliper arm 480 that forces a skid 490 against the wall of a borehole. The magnetic resonance device may be integrated into the skid 490. Electrical communication from a processing device may occur through cable or electronic cartridge 485. One advantage of this design is that the effect of conductive mud may be reduced.

Figure 5:
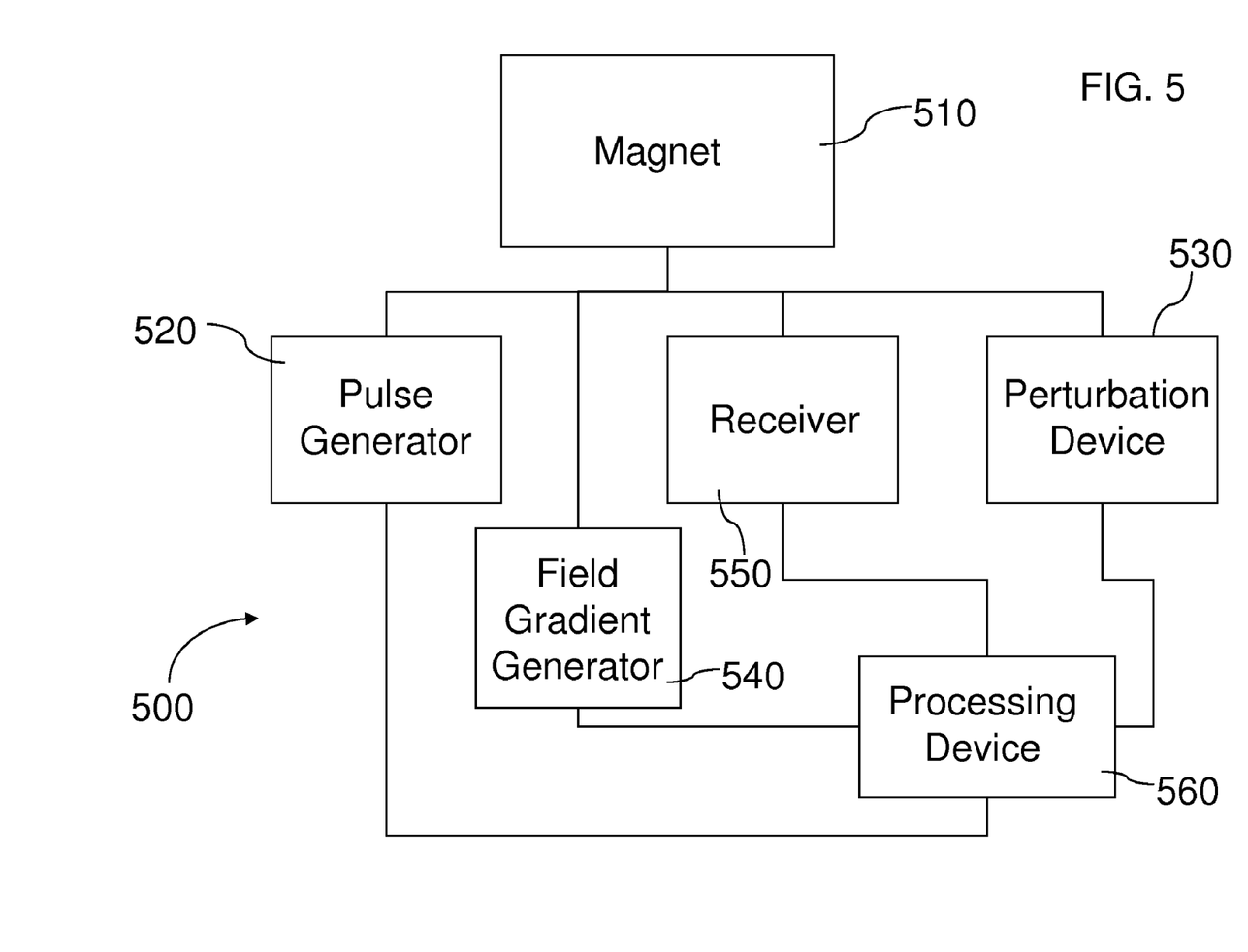
FIG. 5 is a block-diagram of a system including a magnetic resonance device, in accordance with certain examples.

In accordance with certain examples, a system suitable for use with the devices and methods disclosed herein is shown as a block diagram in FIG. 5. The system 500 includes a magnet 510. The magnet 510 is constructed and arranged to produce a static magnetic field. Suitable magnets for use in the devices and systems disclosed herein include, but are not limited to, permanent magnets such as those using rare earth elements (e.g., samarium-cobalt magnets and neodymium-iron-boron magnets), Alnico magnets, ceramic magnets (e.g., strontium and barium ferrite magnets), flexible magnets, and plastic magnets. In other examples, the system may include an electromagnet or a superconducting magnet, particularly where large samples of rock have been removed for analysis uphole.

In accordance with certain examples, the pulse generator 520 may be constructed and arranged to apply a pulse for a suitable time to tip the spins into a desired plane. For example, a radio frequency pulse may be applied for a suitable time to place the spins in the x-y plane or to completely invert the spins. Suitable pulse generators are known in the art, and illustrative pulse generators include, but are not limited to, an antenna, a solenoidal coil, a surface coil, a slotted tube resonator, a loop-gap resonator, a saddle coil, a birdcage coil, and an array of coils or antennas. In examples where the methods, systems and devices disclosed herein are used in downhole applications, the pulse generator is preferably an antenna. Additional suitable devices for generating pulses will be readily selected by the person of ordinary skill in the art, given the benefit of this disclosure. In certain embodiments, the pulse generator may be part of a transmitter/receiver that can apply a pulse and can detect a spin echo.

In accordance with certain examples, the system 500 may also include a device 530 for applying a perturbation. As discussed herein, the perturbation device 530 is operative to induce an oscillation or oscillating fluid flow in a rock formation. The perturbation device may be any of the illustrative devices described herein or other suitable devices that can act to induce an oscillation in a porous medium, such as a rock formation.

In accordance with certain examples, the system 500 may also include a device 540 for providing a magnetic field gradient. An illustrative method for generating a magnetic field gradient includes inducing a voltage in an electrical conductor. For example, one or more gradient coils may be configured to receive a current or voltage to induce a magnetic field in the coil for providing the magnetic field gradient. In other example, a gradient may be produced using an array of permanent magnet assemblies such as those found in a commercially available NMR devices such as Schlumberger's MRX™ tool. An illustrative MRX™ tool is discussed further below and illustrated in FIG. 8. In embodiments where a gradient is provided from an array of permanent magnets, the gradient field strength may be selected by placing the magnet a suitable distance from the rock formation. It will be within the ability of the person of ordinary skill in the art, given the benefit of this disclosure, to select and/or design other suitable devices for applying a magnetic field gradient.

In accordance with certain examples, the system may also include a receiver 550 for detecting a magnetic resonance signal from which a penetration depth of an induced oscillation may be determined. In certain examples, the pulse generator and the receiver may be the same device, e.g., a transmitter/receiver. In other examples, one or more receiver coils may be present to detect a magnetic resonance signal. Additional suitable devices will be readily selected by the person of ordinary skill in the art, given the benefit of this disclosure.

In accordance with certain examples, the, system 500 may also include a processing device 560 that may be electrically coupled to the magnet 510, the pulse generator 520, the perturbation device 530, the field gradient generator 540, and the receiver 550. The processing device 560 may be configured to control the various components of the system, as discussed in more detail herein.

Figure 6:
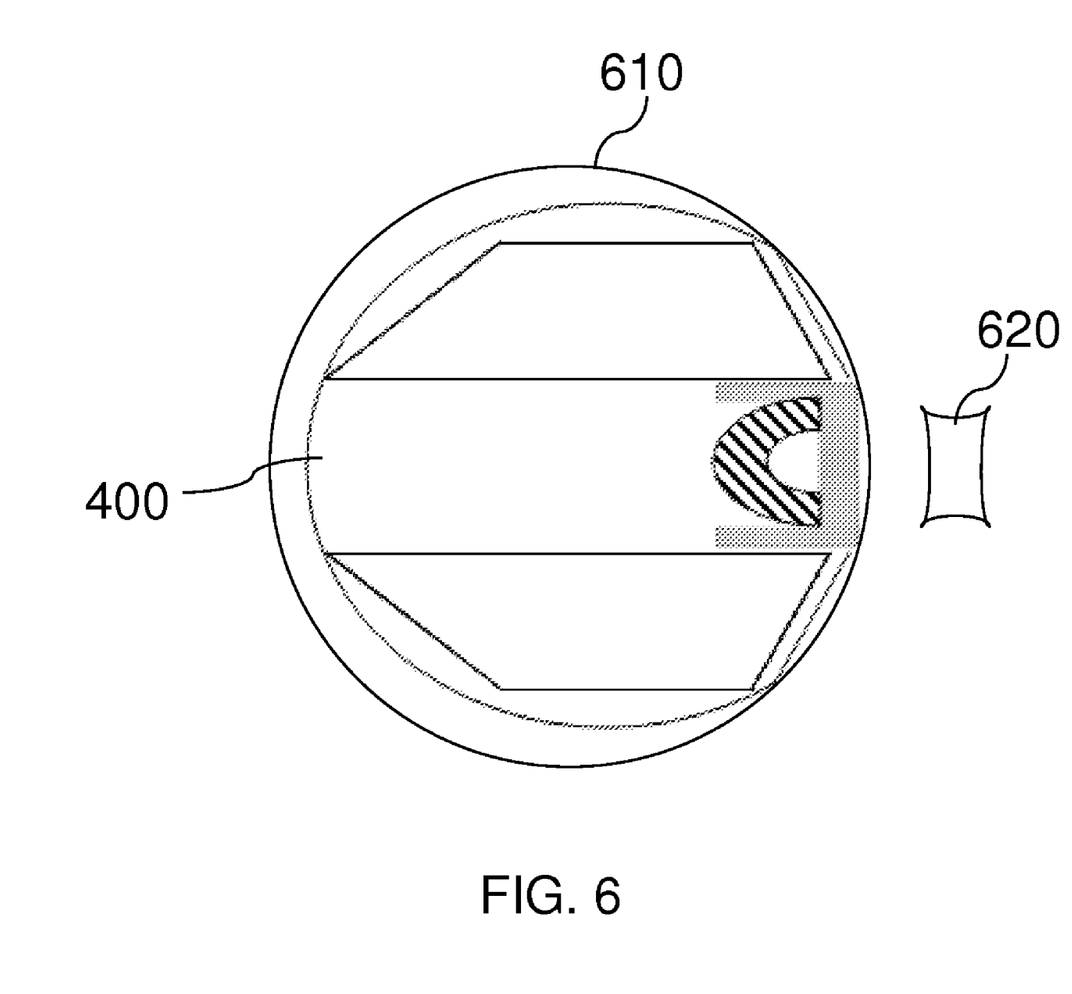
FIG. 6 is a top-view of a magnetic resonance device inserted into a borehole, in accordance with certain examples.

In accordance with certain examples, a location of a rock formation that may be sampled using the device of FIG. 4 is shown schematically in FIG. 6. The device 400, shown in FIG. 6 as being inserted into a borehole 610, provides a sensitive zone 620 in the rock formation. The sensitive zone 620 is the region of the rock formation that is imaged. In using the device shown in FIG. 4, the device is typically inserted into a borehole at a desired position and the spins of the materials in the sensitive zone are allowed to align with the static magnetic field. An external perturbation may be applied to induce an oscillation or oscillatory fluid flow in the sensitive zone. A pulse may be applied to tip the spin into the x-y plane. Alternatively, the pulse may be applied prior to application of the external perturbation. A magnetic field gradient may be applied and phase-locked to the frequency of the perturbation to determine the penetration depth. Repetitive scans may be performed to improve the signal-to-noise ratio and provide a more accurate determination of the penetration depth. The determined penetration depth may then be used to determine a mobility of fluid at that location of the formation. The device may then be moved to a different location and the process may be repeated. This iterative process may take place until a suitable amount of measurements have been made to characterize the rock formations in the borehole. A mobility profile may be produced to assess locations that show promise for producing hydrocarbon fuels.

In accordance with certain examples, once suitable depths within a borehole have been identified the borehole may be prepared for production. One example involves cementing casing into the borehole after the drilling process. The casing areas of the borehole that have high mobility, as identified by penetration depth measurements, may be perforated to provide a path for the hydrocarbon fuels to flow from the rock formation into the production tubing. In certain examples, fluids such as acids and fracturing fluids may be pumped into the well to fracture, clean, or otherwise prepare and stimulate the rock formation to produce hydrocarbons into the wellbore. The hydrocarbons fuels may flow to the surface without aid or downhole pumps, gas lifts, or surface pump-jacks may be used to facilitate extraction of the hydrocarbon fuel sources. It will be within the ability of the person of ordinary skill in the art, given the benefit of this disclosure, to produce well sites identified using the devices, systems and methods disclosed herein.

In accordance with certain examples, a downhole tool is disclosed. In certain examples, the downhole tool comprises a device constructed and arranged to provide a perturbation to induce an oscillation in a porous medium. As discussed herein, the perturbation may take the form of a sound wave, a pressure wave or any form of energy that oscillates and can penetrate a rock formation to at least some degree. Illustrative devices that may be included in the downhole tool to apply a perturbation include a sound generator, a pressure generator, a transducer, a transducer coupled to a Helmholtz resonator, a speaker, a vibrating plate, a piezoelectric device, a resonator tube coupled to a gas source or suitable acoustic devices. The perturbation device is typically located near the rock formation that is being measured such that the perturbations are not distorted, absorbed or otherwise lost from absorption by non-target species, such as drilling fluids and the like. In some examples, the perturbation device may be integrated or packaged with the other components of the downhole tool to facilitate easy insertion of all components into a borehole.

In certain examples, the downhole tool may include a magnetic resonance device constructed and arranged to determine a penetration depth of the induced oscillation. As discussed herein, the magnetic resonance device typically includes a permanent magnet assembly, an antenna for applying pulses and receiving spin echoes and a device for applying a magnetic field gradient to the rock formation. The magnetic resonance device provides a static magnetic field and also provides pulses to manipulate the spins such as tipping them into the x-y plane or inverting them. The magnetic field gradient may be phase-locked with the frequency applied by the perturbation device or a multiple thereof. The magnetic resonance device provides for imaging of the oscillation as it travels into the rock formation and may image the penetration depth of the oscillation.

In certain examples, the downhole tool may also include a processing device electrically coupled to the magnetic resonance device. In some examples, the processing device may be configured to determine the mobility of a fluid in the porous medium from the imaged penetration depth. The processing device typically includes a microprocessor, one or more memory units and associated circuitry, such as buses, a power supply and the like. In certain examples, the processor may be any one or more of those processors typically found in a general-purpose computer such as those based on Unix, Intel PENTIUM-type processor, Motorola PowerPC, Sun UltraSPARC, Hewlett-Packard PA-RISC processors. The processor is typically connected to one or more memory devices, such as a disk drive, memory, or other device for storing data. Components of the processing device may be electrically coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between system components of the processing device. The processing device is typically electrically coupled to the magnetic resonance device so that signals may be received, processed, stored or transferred. In certain examples, the downhole tool may provide data to the processing device, which can relay or transfer data to a central station for further processing and/or viewing. Such transfer allows for real time or near real time monitoring of measurements using the downhole tool. In accordance with certain examples, the processing device may include a display. The display may provide the status of measurements, the results of measurements or other desired parameters. In certain examples, the processing device may also include specially-programmed, special-purpose hardware, for example, an application-specific integrated circuit (ASIC). Aspects of the technology may be implemented in software, hardware or firmware, or any combination thereof. Further, such methods, acts, systems, system elements and components thereof may be implemented as part of the processing device or as an independent component of the downhole tool.

In accordance with certain examples, the processing device may include an operating system for execution of the methods disclosed herein. The operating system may be, for example, Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used, and in certain embodiments a simple set of commands or instructions may function as the operating system. The operating system typically executes one or more programs designed to implement a method for determining penetration depth of an induced oscillation. User input may be prompted to provide various parameters, such as the viscosity of the pore-fluid, porosity, permeability and the effective bulk modulus of the pore-fluid, such that the mobility of a fluid in the rock formation may be determined from the imaged penetration depth of the induced oscillation.

Figure 7:
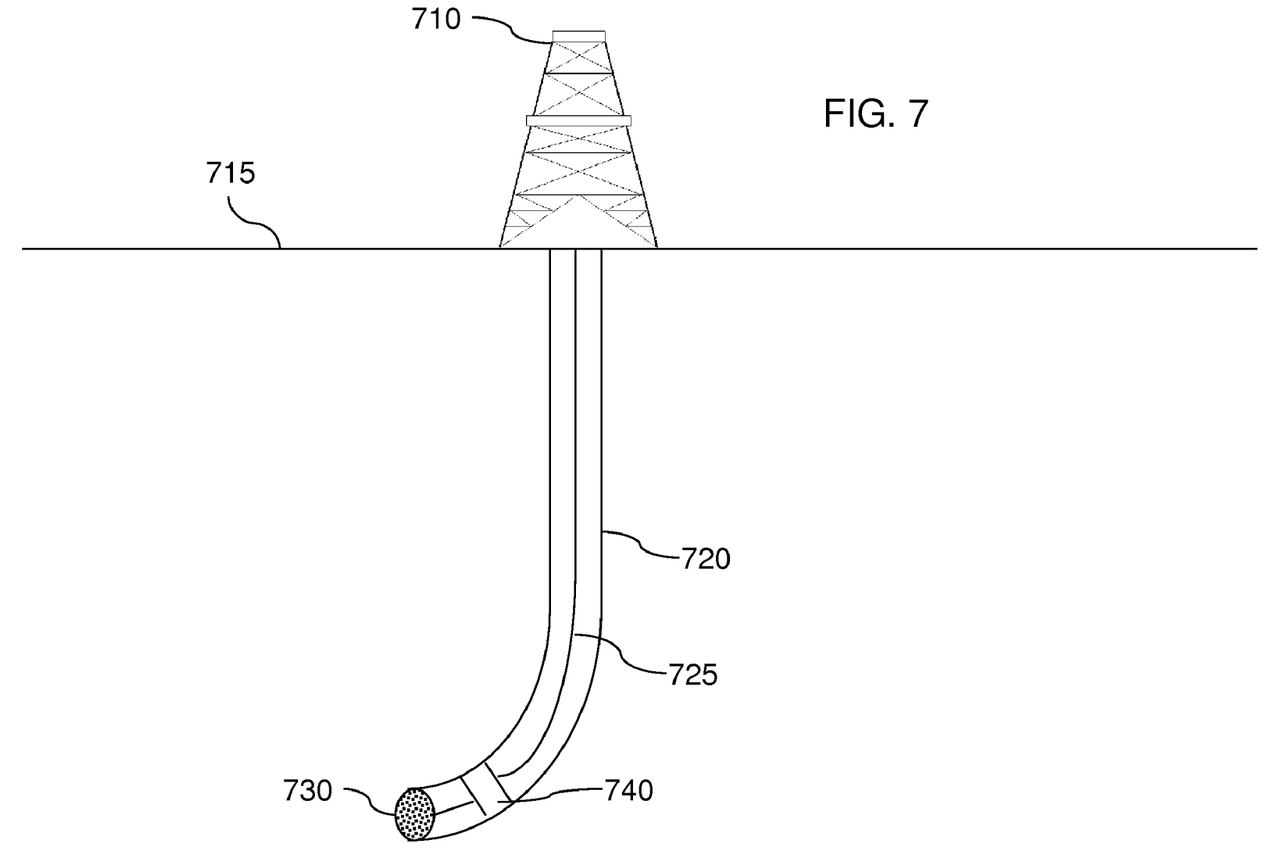
FIG. 7 is an example of a downhole tool in use, in accordance with certain examples.

In accordance with certain examples, an illustrative embodiment of a downhole tool in use with a drilling apparatus is shown in FIG. 7. A drilling rig 710 sits atop a land mass 715 which overlies a borehole 720. The drilling rig 710 has a coupling 725. The coupling 725 may take numerous forms including, but not limited to, a drill string, a wireline, jointed tubing, coiled tubing or other types of strings, tubing and cabling. When drilling is occurring, the coupling 725 is typically a drill string and will be attached to a drill bit 730 and may also couple to a downhole tool 740. When drilling is not occurring, the coupling 725 may be of a different type, including but not limited to a wireline or coiled tubing, and may attach to a downhole tool 740 without the presence of the drill bit 730. The downhole tool 740 is typically configured with a magnetic resonance device. As discussed herein, the downhole tool may apply a radio frequency pulse to tip the spins and a perturbation to induce an oscillation. The perturbation may be followed by application of a magnetic field gradient that is phase-locked to the frequency of the applied perturbation. The downhole tool 740 may then image slices of the rock formation to determine a penetration depth of the induced oscillation. The downhole tool may include an associated processing device to convert the imaged penetration depth into a mobility. Alternatively, the downhole tool may be electrically coupled to a processing device uphole that is configured to receive signals from the magnetic resonance device.

In certain examples, the coupling 725 may also include other analytical devices, drill monitors and the like. For example, a drill motor may be included above the drill bit. An analytical device such as a gas chromatograph may also be included to perform analyses in addition to those described herein. Sensors may be included to measure physical properties in the borehole, e.g., fluid viscosity or to determine drilling direction. It will be within the ability of the person of ordinary skill in the art, given the benefit of this disclosure, to select suitable sensors for use with the devices, systems and methods disclosed herein.

In certain examples, the methods, systems and devices described herein may be used in drilling platforms located off-shore. For example, platform boats, drill boats and the like may be used in ultra deep water drilling applications. The devices, systems and methods disclosed herein are equally applicable in such off-shore drilling applications.

Figure 8:
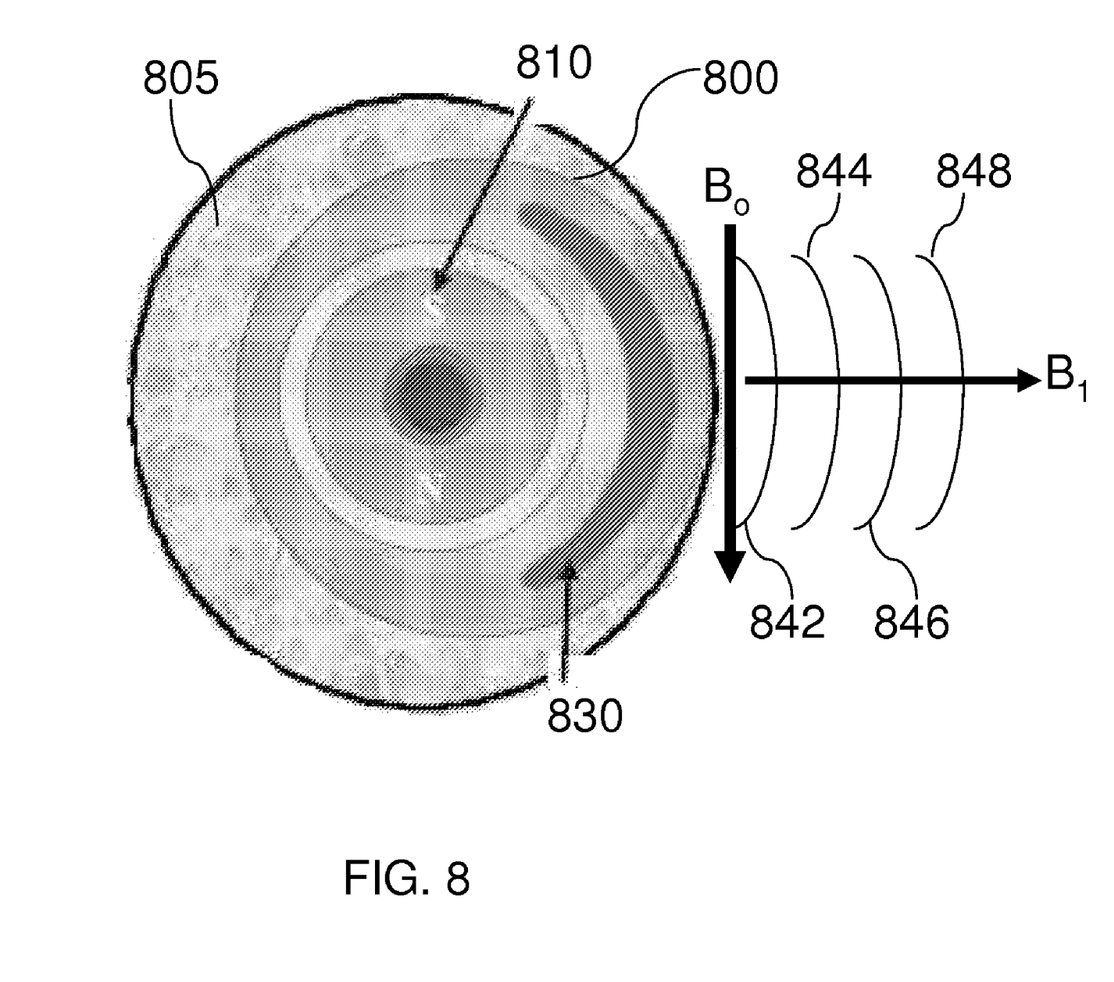
FIG. 8 is another illustrative magnetic resonance device, in accordance with certain examples.

In accordance with certain examples, another magnetic resonance device suitable for use in the devices, systems and methods disclosed herein is shown in FIG. 8. This device is referred to in certain instances herein as an MRX™ device or a MR™ Scanner. The device 800, shown inserted into a borehole 805, includes a permanent magnet assembly 810. The device 800 also includes an antenna 830. The device 800 is configured to sample depths of interest in thin shells, such as shells 842, 844, 846 and 848. Advantages of using the device shown in FIG. 8 may include, but are not limited to, the ability to determine various and multiple depths of interest, the ability to probe deeper into a rock formation, sensing of a large region and easier tuning of the device. The device 800 is also configured to provide both a static magnetic field $B_o$ and a RF field $B_1$. The direction of the static magnetic field $B_o$ and the RF field $B_1$ is shown in FIG. 8. Though shown as being placed next to the surface of a borehole in FIG. 8, the device 800 may perform measurements in the center of the borehole and away from the surface of the rock formation. In particular, the device 800 may be positioned at any radial location from the surface of a rock formation provided that at least two spatially discrete measurements may be taken and used to determine a penetration depth.

In accordance with certain examples, the devices, systems and methods disclosed herein may be used in wireline NMR logging tools used for obtaining information about earth formations and fluids after a wellbore has been drilled. For example, a borehole may be drilled, as discussed above, the drill bit removed, and then the downhole tool may be lowered into the borehole and measurements may be made as the downhole tool travels into the borehole, e.g., at a rate of about 3600 feet/hour. Because rig time is expensive, the goal is to obtain usable data in the least amount of time. Suitable wirelines may connect the magnetic resonance device to computers or systems uphole for data processing and to send instructions downhole to the magnetic resonance device.

In certain examples, the devices, systems and methods disclosed herein may be used to make measurements at selected intervals as the device is being removed from the borehole. For example, the magnetic device may be inserted into a borehole and may be pulled up and out of the borehole at a constant speed, e.g., at about 300-1000 feet/hour. Measurements may be made at a selected interval to obtain magnetic resonance images at various depths in the borehole. The exact interval may vary depending on borehole depth, physical characteristics of the rock and the like. In certain embodiments, a magnetic resonance image may be taken every 0.5 feet, which is a common practice, though other sampling intervals may be used.

In accordance with certain examples, the devices, systems and methods disclosed herein may be used to take measurements as a borehole is being drilled. Such logging while drilling (LWD) or measuring while drilling (MWD) methods can increase the speed by which rock formations are probed for hydrocarbon fuels. It may be desirable to space the magnetic resonance device a suitable distance from the drill bit to avoid or minimize interferences from the drill bit, drilling fluids and the like.

In accordance with certain examples, the devices, systems and methods disclosed herein may be used in station stop measurements. Station stop measurements refer to measurements where the device is positioned at a particular location, held stationary while taking measurements, and then moved to a new location for additional stationary measurements. In certain examples, the stationary measurements may be taken at least about every 10 feet, more particularly every 5 feet, 1 foot or 0.5 feet. Additional intervals for station stops measurements will be readily selected by the person of ordinary skill in the art, given the benefit of this disclosure.

In accordance with certain examples, the devices, systems and methods disclosed herein may be used to assess mobility of a petroleum site after potential petroleum deposits in the site have been rendered mobile. For example, the oil sands in Alberta hold substantial amounts of bitumen impregnated in the sand. This bitumen is generally immobile and not easily extracted. To render the bitumen mobile, steam may be injected into deep oil sands to render the bitumen mobile and capable of extraction. The devices, systems and methods disclosed herein may be used to assess the effectiveness of steam injection to render the bitumen mobile and to select sites for production where high mobility of the bitumen has occurred. In practice, a second well may be drilled below promising wells to allow the mobilized bitumen to drain into the second well. The mobilized bitumen may be pumped from the second well to the surface for processing. So called steam assisted gravity drainage in combination with the technology disclosed herein can increase the efficiency in identifying and extracting hydrocarbons from petroleum bearing formations. In an alternative process, the steam may be replaced with a hydrocarbon solvent to mobilize the bitumen for extraction. The technology disclosed herein may also be used with vapor extraction processes that use such hydrocarbon injection.

In accordance with certain examples, the devices, systems and methods disclosed herein may be used with seismic measurements to assess potential sites for drilling. Such seismic measurement may include active measurements where an explosive is discharged underground or passive measurements made from the surface by detection of, for example, low frequency ambient waves. Other methods of determining where to drill a borehole will be readily selected by the person of ordinary skill in the art, given the benefit of this disclosure.

In accordance with certain examples, the devices, systems and methods disclosed herein may be used to select the most promising sites for production from a plurality of boreholes. Penetration depth measurements may be used to assess which sites have the highest likelihood of easy hydrocarbon fuel extraction. These sites may be produced first to increase the efficiency at which the hydrocarbon fuels are produced.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A method of determining a penetration depth in a porous medium, the method comprising:

inducing at least two oscillations, a first oscillation of at least one pore fluid within the porous medium, and a second oscillation of a magnetic field gradient applied to the porous medium;

analyzing the combined effects of the two oscillations on a magnetic resonance signal so as to determine a penetration depth of the induced first oscillation; and determining the penetration depth of the induced first oscillation from the analyzed magnetic resonance signal.

2. The method of claim 1, wherein the act of determining the penetration depth comprises detecting the magnetic resonance signal that represents an induced oscillatory fluid flow.

3. The method of claim 1, wherein the act of determining the penetration depth comprises determining a depth in the porous medium at which the induced oscillation decays to 1/e.

4. The method of claim 1, further comprising determining a mobility of the at least one pore fluid in the porous medium from the determined penetration depth.

5. The method of claim 1, further comprising determining a permeability of the porous medium from the determined penetration depth.

6. The method of claim 1, wherein the second oscillation includes the magnetic field gradient having an oscillation frequency substantially the same as, or an integer multiple thereof, the frequency of an applied perturbation that generates the induced oscillation, and imaging the induced oscillation using a magnetic resonance device.

7. The method of claim 6, wherein the act of inducing the first oscillation comprises applying the first oscillation as a sound wave.

8. The method of claim 6, wherein the act of inducing the first oscillation comprises applying the first oscillation as a pressure wave.

9. The method of claim 6, wherein the act of detecting the magnetic resonance signal comprises detecting a plurality of magnetic resonance signals as the magnetic resonance device is pulled out of a borehole.

10. The method of claim 6, wherein the act of detecting the magnetic resonance signal comprises detecting a plurality of magnetic resonance signals as the magnetic resonance device is inserted into a borehole.

11. The method of claim 6, wherein the act of detecting the magnetic resonance signal comprises detecting a plurality of magnetic resonance signals as the magnetic resonance device is at a station stop.

12. The method of claim 1, wherein the first oscillation is of a position of magnetic resonance active molecules within the at least one pore fluid within the porous medium.

13. A method of determining a penetration depth of a porous medium by inducing at least two oscillations, a first oscillation is of at least one pore fluid within the porous medium, and a second oscillation is of a magnetic field gradient applied to the porous medium whereby the penetration depth of the induced first oscillation is determined from the analyzed magnetic resonance signal, the method comprising:
determining the penetration depth of an induced oscillatory fluid flow in the porous medium using the magnetic resonance signal from each of two or more spatially discrete points in the porous medium.

14. The method of claim 13, further comprising inducing the oscillatory fluid flow in the porous medium and imaging the induced oscillatory fluid flow in one or more spacial dimensions to determine the penetration depth of the induced oscillation.

15. The method of claim 13, further comprising applying the magnetic field gradient to the porous medium, wherein the magnetic field gradient has substantially the same frequency as the applied perturbation or is an integer multiple thereof.

16. The method of claim 15, wherein the act of using magnetic resonance imaging comprises imaging the induced oscillation with a magnetic resonance device comprising a permanent magnet and a transmitter/receiver.

17. The method of claim 16, further comprising determining a mobility of the at least one pore fluid in the porous medium from the determined penetration depth.

18. The method of claim 13, further comprising determining a permeability of the porous medium from the determined penetration depth.

19. A method for determining formation productivity, the method comprising:
disposing a magnetic resonance device in a borehole near a formation;
inducing at least two oscillations, a first oscillation in at least one pore fluid within the formation, and a second oscillation of a magnetic field gradient applied to the porous medium;
analyzing the combined effects of the two oscillations on a magnetic resonance signal; and
imaging a penetration depth of the induced first oscillation using the magnetic resonance device.

20. The method of claim 19, wherein the act of inducing at least one oscillation of the at least two oscillations comprises inducing an oscillatory fluid flow and wherein the act of imaging further comprises imaging the induced oscillatory fluid flow to determine penetration depth of the at least one oscillation.

21. The method of claim 19, further comprising determining mobility of the at least one pore fluid in the formation from the imaged penetration depth.

22. The method of claim 21, further comprising:
determining a viscosity of the at least one pore fluid in the formation;
determining a porosity of the formation;
determining a permeability of the formation; and
determining the effective bulk modulus of the at least one pore fluid in the formation.

23. A downhole tool comprising:
a device constructed and arranged to induce at least two oscillations, a perturbation to induce a first oscillation in at least one pore fluid within a porous medium and a second oscillation of a magnetic field gradient applied to the porous medium;
a magnetic resonance device constructed and arranged to image a penetration depth of the induced first oscillation by analyzing the combined effects of the two oscillations on a magnetic resonance signal; and
a processing device electrically coupled to the magnetic resonance device, the processing device configured to determine mobility of the at least one pore fluid in the porous medium from the imaged penetration depth.

24. The downhole tool of claim 23, in which the device that is constructed and arranged to provide the perturbation to induce the first oscillation of fluid motion in the porous medium is one or more of a sound generator, a pressure generator, a transducer, a transducer coupled to a Helmholtz resonator, a speaker, a vibrating plate, a piezoelectric device, or a resonator tube coupled to a fluid source.

25. The downhole tool of claim 23, in which the magnetic resonance device comprises a static magnetic field, a device for generating an RF pulse and a device for generating a magnetic field gradient.

26. The downhole tool of claim 23, in which the magnetic resonance device comprises a device for generating both a static magnetic field and a magnetic field gradient and a device for generating an RF pulse.

27. The downhole tool of claim 23, in which the magnetic resonance device is a pulse magnetic resonance tool.

28. The downhole tool of claim 23, in which the processing device is located uphole from the magnetic resonance device.

29. A system for assessing formation productivity, the system comprising:
- a device for inducing at least two oscillations, applying a perturbation to induce a first oscillation in at least one pore fluid within the formation and a second oscillation of a magnetic field gradient applied to the formation;
- a magnetic resonance device comprising a magnet for producing a magnetic field, a transmitter/receiver for applying a radio frequency pulse and for detecting the magnetic resonance signal that represents a penetration depth of the induced first oscillation;
- a device for providing the oscillation magnetic field gradient; and
- a processing device electrically coupled to the magnetic resonance device, the device for applying the perturbation and the device for providing the oscillation magnetic field gradient.

30. The system of claim 29, in which the magnet is a permanent magnet, an electromagnet or a superconducting magnet.

31. The system of claim 29, in which the device for applying the perturbation to induce the first oscillation of the fluid motion in the formation is one or more of a sound generator, a pressure generator, a transducer, a transducer coupled to a Helmholtz resonator, a speaker, a vibrating plate, a piezoelectric device, or a resonator tube coupled to a fluid source.

32. The system of claim 29, in which the device for providing the magnetic field gradient is configured to be phase-locked with the device for applying the perturbation to induce the first oscillation in the formation.

33. The system of claim 29, in which the device for providing the magnetic field gradient is integrated into the magnetic resonance device.

* * * * *